United States Patent [19]

Olive et al.

[11] Patent Number: 4,733,667

[45] Date of Patent: Mar. 29, 1988

[54] CLOSED LOOP CONTROL OF CARDIAC STIMULATOR UTILIZING RATE OF CHANGE OF IMPEDANCE

[75] Inventors: Arthur L. Olive, Stacy; Brian D. Pederson, St. Paul; Rodney W. Salo, Fridley, all of Minn.

[73] Assignee: Cardiac Pacemakers, Inc., St. Paul, Minn.

[21] Appl. No.: 895,241

[22] Filed: Aug. 11, 1986

[51] Int. Cl.$^4$ ............................................. A61N 1/36
[52] U.S. Cl. ............................................. 128/419 PG
[58] Field of Search ............................... 128/419 PG

[56] References Cited

U.S. PATENT DOCUMENTS

| 4,543,963 | 10/1985 | Gessman | 128/419 PG |
| 4,566,456 | 1/1986 | Konig et al. | 128/419 PG |
| 4,567,892 | 2/1986 | Plicchi et al. | 128/419 PG |
| 4,674,518 | 6/1987 | Salo | 128/419 PG |

Primary Examiner—William E. Kamm
Attorney, Agent, or Firm—Orrin M. Haugen; Thomas J. Nikolai; Frederick W. Niebuhr

[57] ABSTRACT

A cardiac pacer of the type having an implantable pulse generator and electrical leads deployed in the right ventricular chamber of the heart. The lead has a stimulating electrode as well as a plurality of sensing electrodes coupled to the pulse generator. Certain control circuitry associated with the implantable pacer provides for measurement of the impedance variations occasioned by the pumping action of the heart and a differentiating circuit operatively coupled to the impedance sensing circuit for developing a control signal corresponding to the rate of change of the impedance with respect to time. This control signal may be coupled to the timing circuit of the implantable pulse generator, allowing the pacing rate to be altered in accordance with the level of physiologic activity of the person in whom the pacer is implanted.

7 Claims, 7 Drawing Figures

(a) IMPEDANCE SIGNAL R(t)

(b) DERIVATIVE OF IMPEDANCE R'(t)

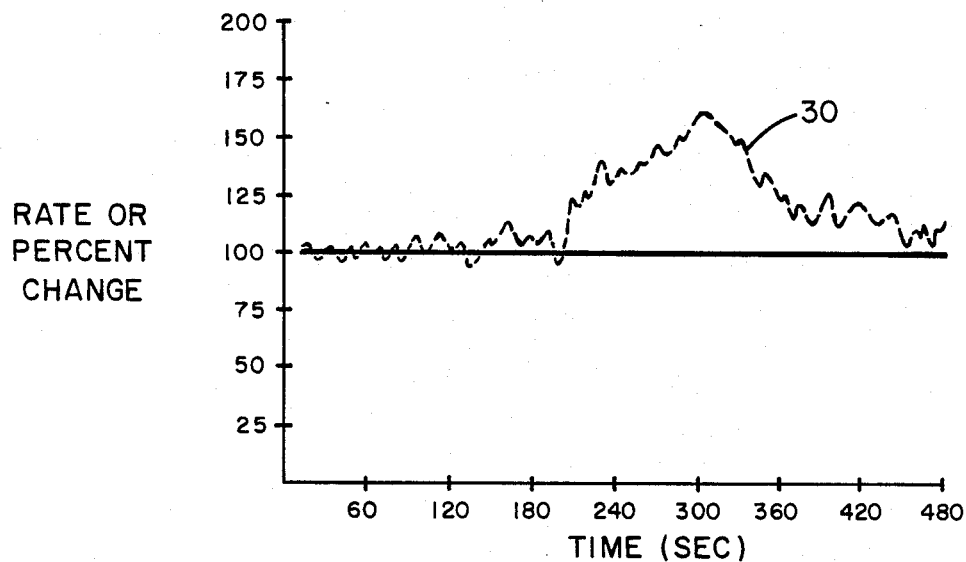
_Fig. 4_
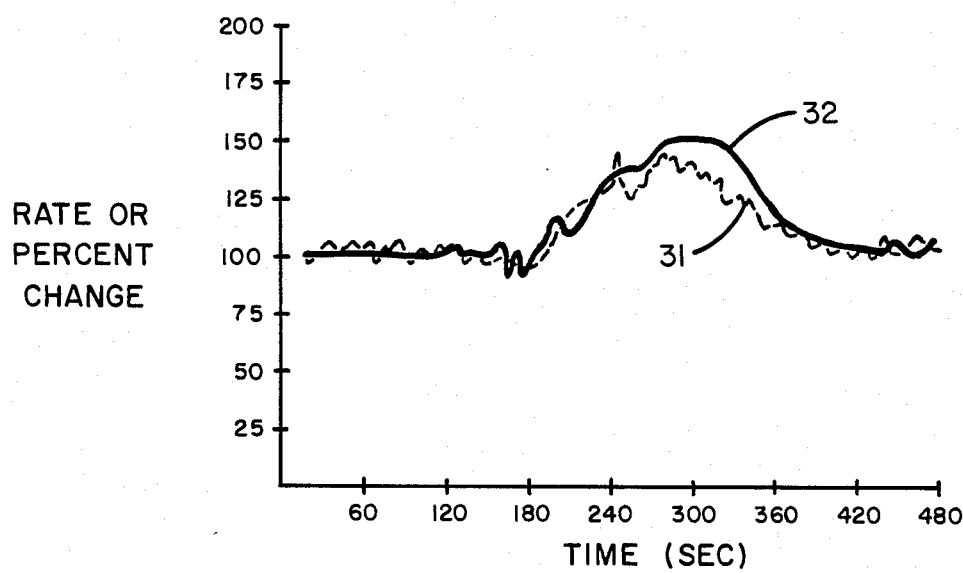
_Fig. 5_

CLOSED LOOP CONTROL OF CARDIAC STIMULATOR UTILIZING RATE OF CHANGE OF IMPEDANCE

BACKGROUND OF THE INVENTION

I. Field of the Invention: This invention relates generally to cardiac pacemakers, and more particularly to the design of a cardiac pacemaker in which the stimulation rate is under closed loop control and varies in accordance with the contractility of the heat.

II. Discussion of the Prior Art: In accordance with the teachings of an earlier invention described in application Ser. No. 362,903, filed Mar. 29, 1982, and entitled "BIOMEDICAL METHOD AND APPARATUS FOR CONTROLLING THE ADMINISTRATION OF THERAPY TO A PATIENT IN RESPONSE TO CHANGES IN PHYSIOLOGIC DEMAND" (now U.S. Pat. No. 4,686,987), there is disclosed a system for measuring absolute and relative variations in the impedance of the heart, related to the instantaneous stroke volume, and using that impedance signal to control the admistration of medically-related therapy to the patient. In that application, there is described an implantable lead arrangement and associated circuitry whereby, using impedance plethysmography, the instantaneous impedance measured in a chamber of a beating heart can be sensed and used to vary or adjust the pacing rate of an implantable cardiac pacemaker. A drawback of this earlier invention is that under certain circumstances the normal rate response to changes in stroke volume are reversed. For example, when a patient stands up, his stroke volume decreases which would normally result in a decreased pacing rate. However, an increase in rate is necessary to prevent postural hypotension. Thus, a pacing system based only on stroke volume may not respond optimally in all situations.

In addition to positional sensitivity, the control signal proportional to absolute or relative right ventricular impedance (or stroke volume) obtained using the system of the aforereferenced application is rate dependent. While this allows a fairly sophisticated "closed loop" pacing system to be developed, these systems are necessarily more complex than simple "open loop" systems. Thus, a control parameter which is independent of pacing rate would be attractive in that it would allow the use of simpler, and presumably smaller and cheaper, control circuitry.

Finally, an appropriate independent signal can be used in concert with the impedance stroke volume signal of the invention described in U.S. Pat. No. 4,686,987 to resolve the aforementioned ambiguities as to the desired direction of rate change.

In the Koning et al U.S. Pat. No. 4,566,456, there is described a cardiac pacer incorporating means for sensing right ventricular systolic pressure and then using that pressure value to develop a control signal for adjusting the escape interval of an implanted cardiac pacer. In the introductory portion of that patent, there is briefly described other prior art patents and publications relating to pacemaker designs in which the pacing rate is automatically adjusted to accommodate the patient's level of physical activity. The implementation disclosed in the Koning patent as well as those described in certain of the other patents referenced therein require a fairly complex and, as yet, totally unproven sensor. The pressure transducer of Koning, for example, would necessarily be affected by fibrotic encapsulation which would necessarily significantly alter the manner in which the pacer's escape interval is made to vary with exercise within a relatively short time following implantation.

SUMMARY OF THE INVENTION

In accordance with the present invention, we have found that the problems due to positional changes of the patient can be obviated by using the average peak value of the first derivative of the impedance waveform as the control signal to be used in modifying the timing cycle of the pacemaker. That signal shall be identified herein as $(dZ/dt)p$. Studies to date have shown that $(dZ/dt)p$ tends to be independent of pacing rate and is directly proportional to the contractility of the heart. The heart's contractility is, in turn, a function of the catecholamine level in the blood and the degree of activation of the sympathetic nervous system, both of which vary with exercise. Thus, $(dZ/dt)p$ is an excellent signal to be used on a closed loop basis for governing the timing interval of a cardiac pacer. Further, because $(dZ/dt)p$ has been found to be relatively independent of pacing rate, this factor can be directly mapped over into the pacing period which simplifies the circuit implementation.

In carrying out the invention, a catheter or lead having a stimulating tip electrode and a plurality of drive and sense electrodes is inserted into the right ventricle of the heart and a signal of a predetermined frequency is applied between the tip or other distal electrode and a more proximal ring electrode. A sensing amplifier is then connected across two ring electrodes spanned by the drive electrodes or the drive electrodes themselves, and it is found that the beating action of the heart results in modulation of the applied carrier signal. Circuitry is used to remove the envelope and the peak-to-peak amplitude of the resulting impedance waveform is directly proportional to the heart's stroke volume. This impedance waveform is then applied to a differentiation circuit which produces an output proportional to the first derivative of the impedance waveform $(dZ/dt)$ on a beat-by-beat basis. This latter signal is applied to a peak detector and the peak value applied to an algorithm such that the pacing cycle length is decreased with increases in $(dZ/dt)p$.

In that the $dZ/dt$ measurement can be made from a standard pacing lead or from a pacing lead including only one additional surface ring electrode thereon, the present invention can be practiced without resorting to exotic sensors. Also, the lead system used to obtain the $dZ/dt$ parameter, unlike the pressure transducer in the Koning et al patent, is unaffected by fibrotic encapsulation and, therefore, there is no long-term degradation of performance of the pacer. Also, since a relatively standard pacing lead can be used to derive the $dZ/dt$ information, the pacer of the present invention can be used during pacemaker replacement in those patients who already have a pacing lead in the ventricle without subjecting them to the trauma and risk of explanting their current lead.

OBJECTS

It is accordingly a principal object of the present invention to provide an improved closed-loop cardiac pacer whose pacing rate varies with the level of exercise of the patient.

Another object of the invention is to provide in a closed-loop cardiac pacer a method of operation in which the pacing rate is made to vary with the rate of change of ventricular impedance.

Yet another object of the invention is to provide a demand-type cardiac pacemaker which includes means for developing a control signal proportional to the peak value of the rate of change of intracardiac impedance measured on a beat-to-beat basis and using that control signal to vary the escape interval of the pacer.

Still another object of the invention is to provide a physiologic pacer which uses conventional endocardial pacing leads in its implementation.

These and other objects and advantages of the invention will become apparent to those skilled in the art from the following detailed description of a preferred embodiment, especially when considered in conjunction with the accompanying drawings.

DESCRIPTION OF THE DRAWINGS

FIG. 2 waveform (b) is a trace showing the derivative of the impedance dZ/dt with the peak amplitude (dZ/dt)p indicated by "C".

FIG. 4 is a curve showing the manner in which the peak dZ/dt signal varies with changes in the level of exercise but with a fixed pacing rate.

FIG. 5 is a curve showing the closed loop rate controlled pacer utilizing a signal proportional to (dZ/dt)p as the escape interval adjusting control signal.

DESCRIPTION OF THE PREFERRED EMBODIMENT

Figure 1:
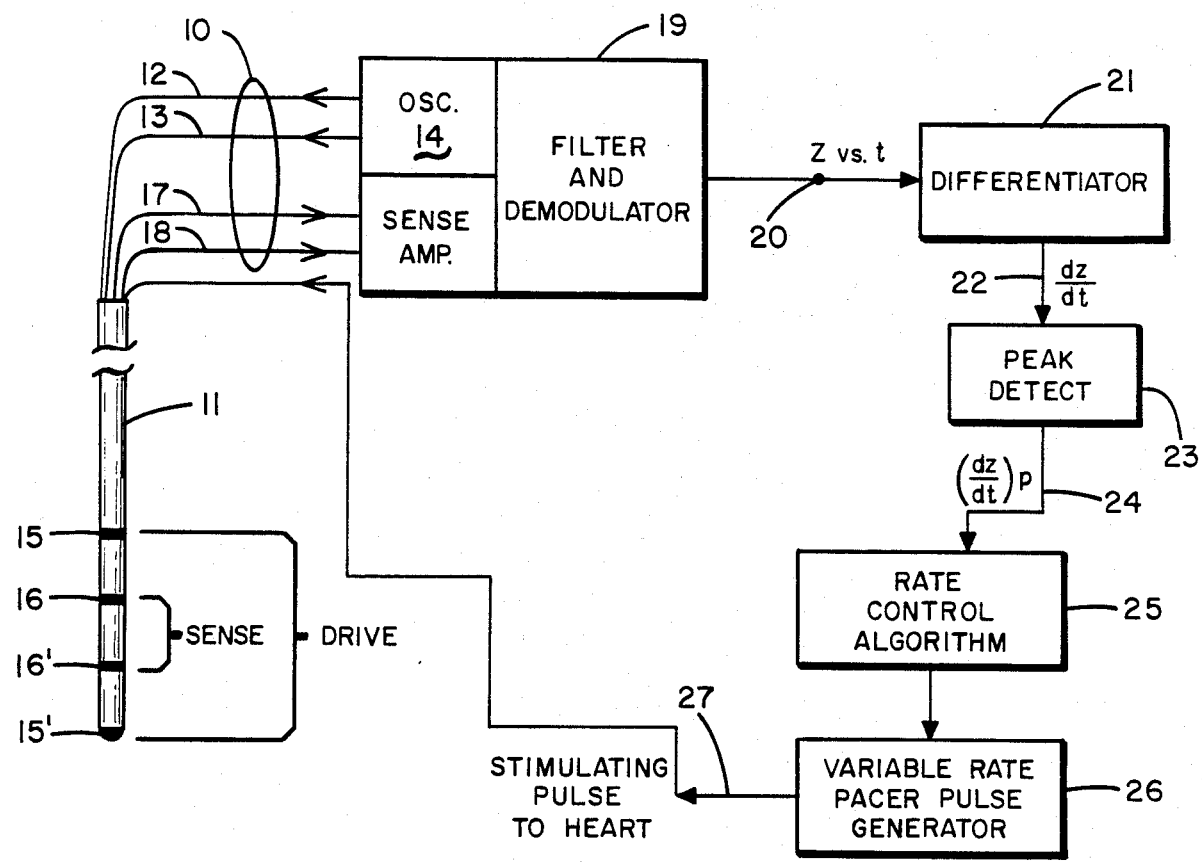
FIG. 1 is a block diagram representation of the preferred embodiment.

In FIG. 1 there is shown by means of a block diagram a preferred embodiment of the cardiac stimulating apparatus incorporating the present invention. Identified by numeral 10 are conductors which extend through a suitable catheter 11 into the heart and, preferably, its right ventricle. In accordance with the above-referenced U.S. No. 4,686,987, the electrical conductors 12 and 13 are used to couple the output of a carrier oscillator circuit 14 to predetermined electrodes 15 and 15' mounted on the surface of the catheter. These would be the so-called drive electrodes, and disposed between the drive electrodes on the catheter body are a pair of spaced-apart sense electrodes 16 and 16' which are coupled by electrical wires extending the length of the catheter body and are joined to the pacer electronics as indicated by input lines 17 and 18.

The impedance waveform generator 19 would include amplifying, filtering and demodulating circuitry, such as of the type more particularly explained in the aforereferenced U.S. Pat. No. 4,686,987.

Thus, the signal appearing on output point 20 from the impedance waveform generator is a time-varying signal corresponding to the impedance measured between the two spaced-apart sense electrodes within the heart. That signal is applied as an input to a differentiator network 21, many implementations of which are common in the electronics arts. A signal proportional to the first derivative of the impedance waveform thus results on output line 22, and that signal is applied to a peak detector 23 where the peak value of the first derivative of the impedance waveform is captured on a beat-by-beat basis whereby the signal on output line 24 is proportional to the peak value of dZ/dt. It is this signal that is then used to control the esape interval of the pacemaker pulse generator. In that (dZ/dt)p increases during exercise because of the increase in contractility of the heart due to the concomitant increase in catecholamine levels in the blood and the response of the sympathetic nervous system to exercise, the conversion algorithm may be the solution to the equation:

$$EI = B - A((dZ/dt)p - (dZ/dt)p^{REST})  \quad (EQ.1)$$

where EI is the escape interval, A is a gain or sensitivity factor which depends upon the characteristics of the sensor being employed and the units involved and "B" is the escape interval at rest and $(dZ/dt)p^{REST}$ is the average value of (dZ/dt)p measured with the patient at rest. The computation comprising the rate control can readily be algorithm 25 carried out in a special purpose digital control logic device. The output of the variable rate pacer 26 on line 27 is applied through the catheter or pacer lead 11 to the tip electrode 15'.

Figure 2:
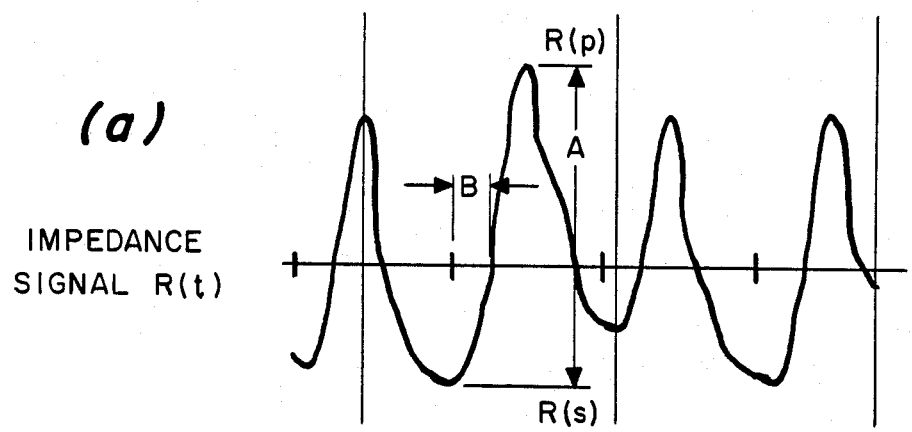
FIG. 2 waveform (a) shows a typical impedance waveform with the peak-to-peak amplitude shown as "A", proportional to stroke volume.
Figure 2:
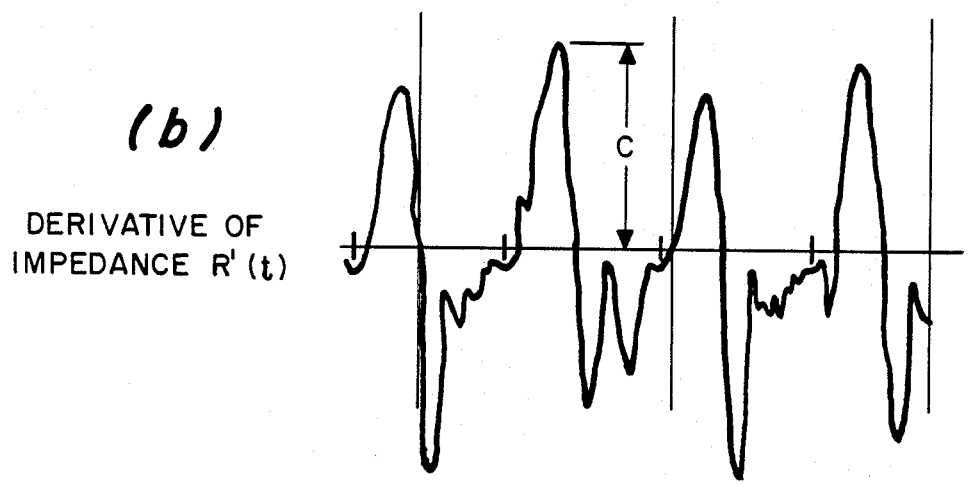

In FIG. 2 waveform (a) represents a typical impedance signal obtained using the apparatus corresponding to block 19 in FIG. 1 where the peak-to-peak amplitude is identified as "A".

In FIG. 2 waveform (b) depicts the first derivative of the curve of waveform with the peak amplitude identified as "C".

Figure 3:
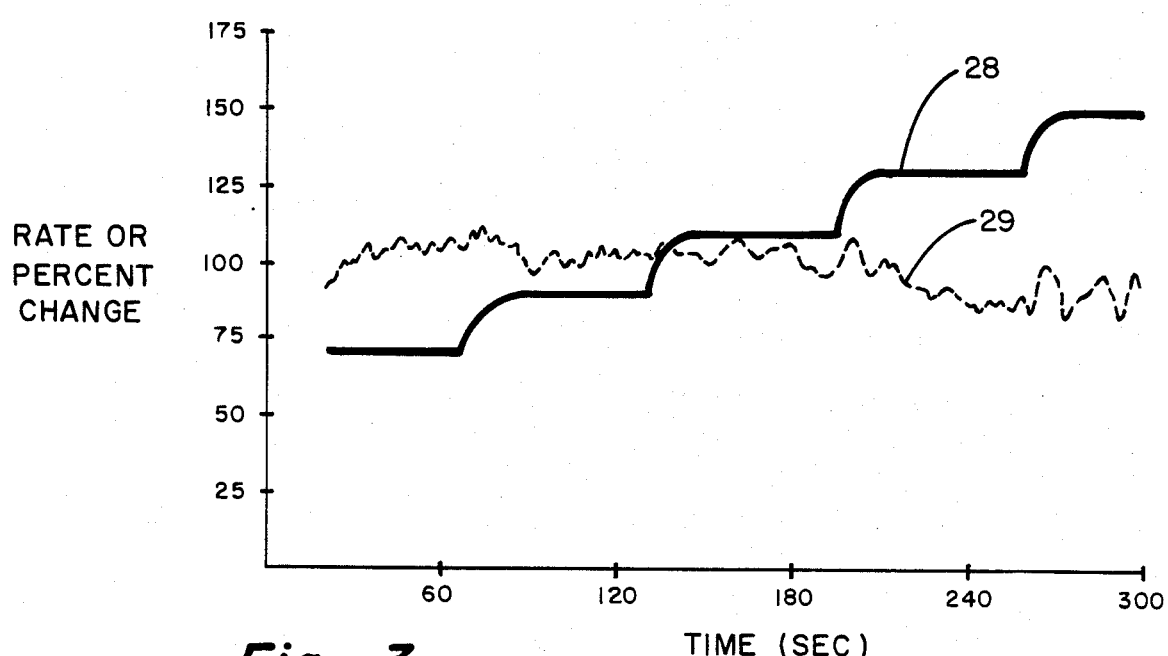
FIG. 3 comprises a waveform showing the manner in which the control signal developed in FIG. 1 remains fairly constant with changes in pacing rate when the subject is at rest.

The curves of FIG. 3 show the relationship between pacing rate and the dZ/dt peak. In this figure, pacing rate in beats-per-minute and percent change in (dZ/dt)p from a 100% baseline are plotted on the same ordinate axis. In gathering the data reflected in FIG. 3, an impedance plethysmography catheter was placed in the right ventricle of a dog and then the dog's heart was paced for one minute periods at different increasing frequencies. The curve 28 indicates that, for approximately the first minute of the test, the dog's heart was being paced at approximately 70 beats-per-minute and that the pacing rate was then increased to approximately 90 beats-per-minute, then to 110, 130 and 150. The wave 29 in FIG. 3 is the measured peak values of the dZ/dt and, as can be seen, remains relatively constant with changes in pacing rate when the dog is not being exercised.

FIG. 4 shows the fixed rate response of the dZ/dt controlled pacer operating in open-loop mode with the pacing rate held constant at approximately 100 beats-per-minute but with the level of exercise changing. The dog in question was placed on a treadmill and, at intervals of one minute, the level of exertion was increased. More particularly, the experiment began at time equal to 120 seconds with the dog being exercised at a 3 miles per hour rate. After one minute, the level of exercise was raised to 7 miles per hour and then after one minute, the level of exercise was raised to 10 miles per hour. The exercise was terminated at the conclusion of five minutes. The waveform 30 shows the manner in which the (dZ/dt)p factor varies as a function of workload and measured relative to a 100% baseline. As was earlier indicated, that factor is a direct function of the contractility of the heart so that the higher the rate of exercise, the greater the magnitude of (dZ/dt)p. The waveforms of FIG. 5 illustrate the variation in pacing rate when the (dZ/dt)p is used to control the pacing rate. Rather than pacing the dog's heart at a constant rate as indicated in FIG. 3, the pacing rate was allowed to vary as a function of exercise level as measured by the apparatus of FIG. 1. FIG. 5 shows that, as the dZ/dt factor increased with exercise relative to the 100% baseline (curve 31), the pacing rate measured in beats-per-minute also increased as indicated by curve 32.

In that the control factor (dZ/dt)p is relatively independent of pacing rate (FIG. 3), it becomes a fairly easy matter to implement a conversion scheme across the entire range of pacing rates possible. The above equation for the escape interval, EI, above illustrates the simplicity of the expression for the conversion algorithm whereby the dZ/dt peak may be used to adjust the pacer's pulse period.

Figure 6:
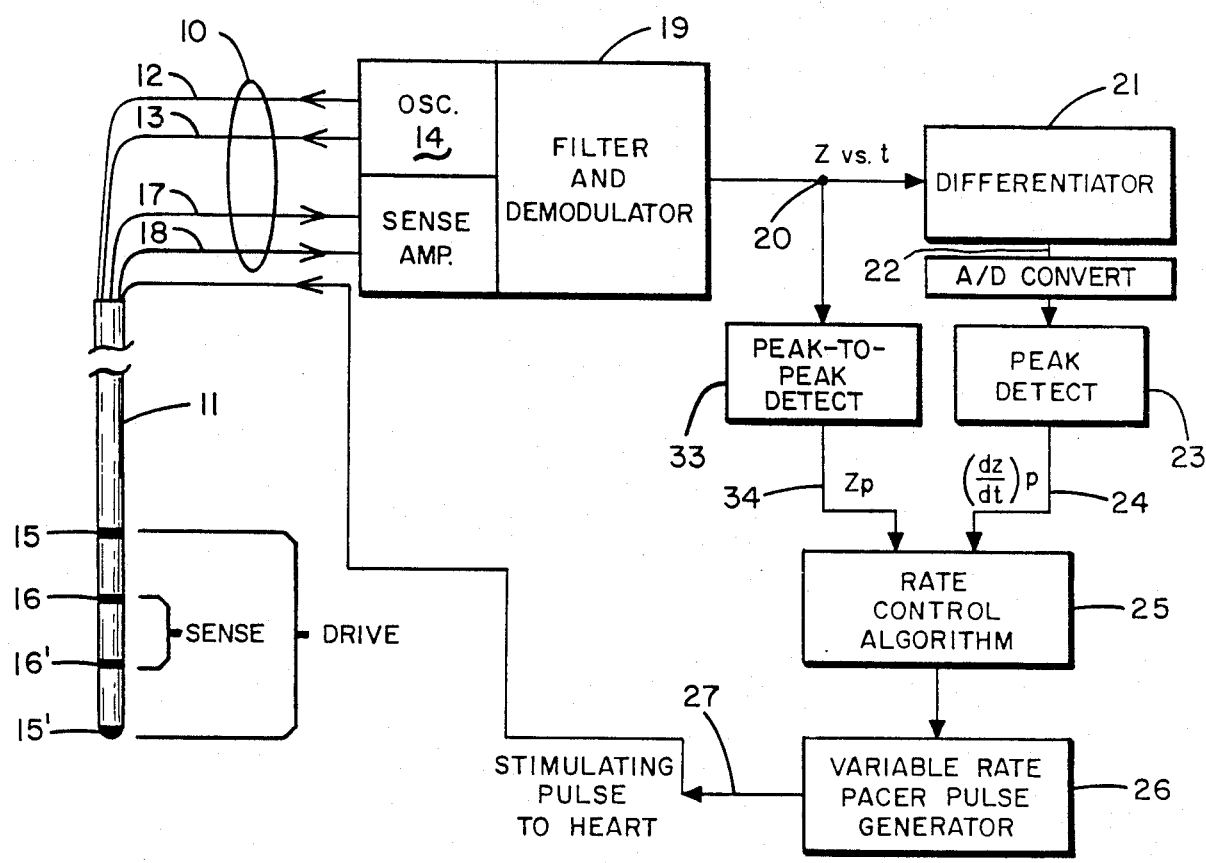

Referring next to FIG. 6, an alternative to the embodiment thus far described can be obtained by including a peak-to-peak detector 33 for receiving the Z vs. t signal at point 20 and applying the average peak-to-peak value thereof to the rate control algorithm 25 in conjunction with (dZ/dt)p appearing on line 24. Here, rather than following the expression defined by equation 1 above, the escape interval may be determined instead by the equation:

$$EI = B - A \, ((Z)p - (Z)p^{REST}) \qquad \text{(EQ. 2)}$$

where $(Z)p$ is the peak-to-peak value of the impedance waveform (a) of FIG. 2 and $(Z)p^{REST}$ is the average peak-to-peak value of the measured impedance with the patient at rest. Again, A is a gain or sensitivity factor which depends upon the characteristics of the sensor being employed and the units involved and "B" is the escape interval at rest. The (dZ/dt)p signal on line 24 in FIG. 6 is used to determine the direction that the escape interval is to be changed. Specifically, if the (Z)p signal appearing at the output of the peak-to-peak detector 33 on line 34 is increasing at the same time that the (dZ/dt)p signal on line 24 is increasing, the rate control algorithm 25 operates such that there is an increase in the pacing rate, i.e., a reduced escape interval. If, on the other hand, the signal on line 34 increases while that on line 24 decreases, the pacing rate should be made to decrease for a predetermined interval, because that is the condition one would expect to occur when the patient lies down to rest. If it is determined by the rate control algorithm 25 that both the signals on lines 24 and 34 are decreasing, then the algorithm functions to increase the escape interval, i.e., decrease the pacing rate. Finally, if the signal on line 34 is decreasing while that on line 24 is increasing, it is desirable that the pacing rate be increased in that this is the condition that prevails when the patient stands up after having been in a reclining position for a prolonged period. Again, the time constant involved should be short, e.g., only about one minute. This would tend to compensate for the sudden light-headedness which may result when an individual suddenly assumes a standing position following a prolonged interval in a reclining position.

In actually implementing the present invention, it is possible to use all analog circuitry or, alternatively, by incorporating an analog-to-digital converter circuit in the line 22 between the differentiator 21 and the peak detector 23, the signal proportional to dz/dt can be digitized which may tend to facilitate the peak detection as well as the conversion algorithm.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed is:

1. An adjustable rate cardiac pacemaker comprising in combination:

sensing means for sensing intracardiac impedance on a beat-by-beat basis and producing a time varying signal representation thereof;

differentiating means coupled to said sensing means for forming the first derivative of said time varying signal;

peak detecting means coupled to said differentiating means for detecting the peak amplitude of the differentiated signal on each beat and producing a time varying control signal in relation thereto; and variable rate pulse generating means coupled to receive said time varying control signal.

2. The adjustable rate cardiac pacemaker as in claim 1 wherein said sensing means comprises:

an intracardiac electrical lead for placement in a ventricular chamber and having proximally located terminal means and an insulating lead body with at least two electrodes disposed at spaced apart locations along the surface thereof such that when said electrical lead is inserted into the heart, said two electrodes are resident in one ventricular chamber of the heart, said electrodes being electrically coupled to said terminal means;

carrier oscillator means for producing a drive signal of a predetermined frequency coupled to said terminal means;

sense amplifier means having its input coupled to said terminal means for sensing the modulation of said drive signal occasioned by the beating action of the heart; and demodulating means coupled to said sense amplifier means for recovering the modulation signal from the modulated drive signal.

3. The adjustable rate cardiac pacemaker as in claim 1 wherein said sensing means comprises:

an intracardiac electrical lead having terminal means at its proximal end, an insulating lead body with a pair of drive electrodes disposed at spaced apart locations along the surface of said lead body such that when said lead is operatively disposed in a ventricular chamber at least one of said drive electrodes is within said ventricular chamber of the heart, and a pair of sense electrodes disposed on the surface of said lead body and between said drive electrodes, each of said sense electrodes being resident within said ventricular chamber when said lead is operatively disposed within said ventricular chamber, each of said electrodes being connected by individual conductors to said terminal means at the proximal end of said lead;

carrier oscillator means for producing a drive signal of a predetermined frequency coupled to the ones of said terminal means associated with said drive electrodes;

sense amplifier means having its input coupled to ones of said terminal means associated with said sense electrodes for sensing the modulation of said drive signal occasioned by the beating action of the heart; and demodulator means for receiving the modulation signal from the modulated drive signal.

4. An adjustable rate cardiac pacemaker comprising, in combination:

sensing means for sensing intracardiac impedance on a beat-by-beat basis and producing a time varying signal representation thereof;

differentiating means coupled to said sensing means for forming a rate of change signal directly proportional to the first derivative of said time varying signal;

peak detecting means coupled to receive said time varying signal and said rate of change signal for detecting the peak values of each of said signals on beat-by-beat basis and producing an output in relation thereof; and means in said cardiac pacemaker for altering the rate at which heart stimulating pulses are generated by an amount determined by the peak-to-peak value of the sensed intracardiac impedance and in a direction (increase or decrease) determined by the peak value of said rate of change signal.

5. A method of controlling the rate at which cardiac stimulating signals are produced by a cardiac pacemaker of the type having a variable rate pulse generator comprising the steps of:

(a) sensing the stroke volume of the heart on a beat-to-beat basis and developing a time varying signal directly proportional thereto;

(b) differentiating said time varying signal to produce a signal corresponding to the first derivative of said time varying signal;

(c) developing a control signal directly proportional to the peak value of said first derivative of said time varying signal;

(d) applying the peak-to-peak value of said time varying signal to said pulse generator for varying the rate at which stimulating signals are generated; and (e) applying said control signal to said pulse generator for determining the direction in which the rate is to be varied.

6. The method as in claim 5 wherein sensing of the stroke volume is accomplished by measuring the intracardiac impedance.

7. The method as in claim 6 wherein the step of measuring the intracardiac impedance is performed by applying an AC drive signal of a predetermined frequency as a carrier across spaced-apart electrodes contained within the ventricular chamber of the heart and sensing the resulting modulation of said carrier occasioned by the beating action of the said heart.

* * * * *